United States Patent
Lehenberger et al.

(10) Patent No.: US 10,390,946 B2
(45) Date of Patent: *Aug. 27, 2019

(54) METHOD FOR THE PREPARATION OF BIOLOGICAL TISSUE FOR DRY USE IN AN IMPLANT

(71) Applicant: BIOTRONIK AG, Buelach (CH)

(72) Inventors: Nina Lehenberger, Fuerth (DE); Alexander Rzany, Nuremberg (DE); Wilhelm Erdbruegger, Constance (DE)

(73) Assignee: Biotronik AG, Buelach (CH)

( * ) Notice: Subject to any disclaimer, the term of this patent is extended or adjusted under 35 U.S.C. 154(b) by 580 days.

This patent is subject to a terminal disclaimer.

(21) Appl. No.: 14/671,112

(22) Filed: Mar. 27, 2015

(65) Prior Publication Data

US 2015/0282930 A1    Oct. 8, 2015

(30) Foreign Application Priority Data

Apr. 2, 2014 (EP) .................... 14163120

(51) Int. Cl.
*A61F 2/24* (2006.01)
*A61L 27/36* (2006.01)

(52) U.S. Cl.
CPC .......... *A61F 2/2418* (2013.01); *A61F 2/2427* (2013.01); *A61L 27/367* (2013.01); *A61L 27/3625* (2013.01); *A61L 27/3687* (2013.01); *A61F 2240/001* (2013.01); *A61L 2400/02* (2013.01); *A61L 2400/18* (2013.01); *A61L 2430/20* (2013.01)

(58) Field of Classification Search
None
See application file for complete search history.

(56) References Cited

U.S. PATENT DOCUMENTS

| 4,357,274 A | 11/1982 | Werner |
| 2009/0324684 A1 | 12/2009 | Atanasoska et al. |
| 2010/0030340 A1* | 2/2010 | Wolfinbarger, Jr. ........ A61F 2/4644 623/23.72 |
| 2012/0143227 A1 | 6/2012 | Steckel et al. |
| 2013/0158658 A1 | 6/2013 | Hayzlett |
| 2017/0119928 A1 | 5/2017 | Rzany et al. |

FOREIGN PATENT DOCUMENTS

| EP | 2668966 A1 | 12/2013 |
| EP | 2893905 A1 | 7/2015 |
| EP | 2926840 | 10/2015 |
| WO | 1999/66967 A1 | 12/1999 |
| WO | WO 99/66967 | * 12/1999 |
| WO | WO 2004/052417 | * 6/2004 |
| WO | WO2005/024099 A1 | 3/2005 |

OTHER PUBLICATIONS

EP14163120.0 European Search Report dated Aug. 28, 2014.

* cited by examiner

*Primary Examiner* — Erin M. Bowers
(74) *Attorney, Agent, or Firm* — Wagenknecht IP Law Group PC

(57) ABSTRACT

A method of preparing biological tissue for use as a component of an implant, in particular as part of a heart valve prosthesis, which can be implanted by catheter. The biological tissue is subjected to a dimensional and structural stabilization step and is dried. For the dimensional and structural stabilization, a combination of a first, polyethylene glycol-containing solution and at least one second, glycerol-containing solution is used.

16 Claims, 2 Drawing Sheets

METHOD FOR THE PREPARATION OF BIOLOGICAL TISSUE FOR DRY USE IN AN IMPLANT

CROSS REFERENCE TO RELATED APPLICATIONS

This application claims benefit of priority to European patent application no. EP 14163120.0 filed Apr. 2, 2014; the content of which is herein incorporated by reference in its entirety.

TECHNICAL FIELD

The present invention relates to a method for the preparation of biological tissue for use as a component of an implant, in particular for use as a component of a heart valve prosthesis, and to an implant, which contains a thusly prepared biological tissue in the dried state.

BACKGROUND OF THE INVENTION

The invention is described in the following using the example of a method for preparing tissue for use for an artificial heart valve. Although the present invention is particularly suitable for preparing this type of tissue, it is not limited to this application. The present invention can also be used to prepare blood vessels, skin tissue, ligaments, or the like.

There are basically two different types of heart valve prostheses: mechanical valves, which are artificially produced, usually being made of graphite coated with pyrolytic carbon; and biological prostheses, which are often made of pericardial tissue, which is usually obtained from animal sources (e.g. swine or cattle). The heart valve formed of biological tissue is usually mounted in a base body (e.g. a rigid plastic framework or a self-expanding stent), which is then implanted at the position of the natural valve. The present invention describes a method for preparing such tissue for use in a heart valve prosthesis, which performs the function of a natural heart valve.

The tissue of origin must be thoroughly cleaned and prepared before implantation. In so doing, the tissue is modified, to the greatest extent possible, such that the tissue is not recognized by the body as foreign tissue, is not calcified, and has the longest life span possible. Such a method for the preparation of tissue substantially comprises a plurality of steps.

One possible preparation step is the so-called decellularization of the tissue. In this step, cell membranes, intracellular proteins, cell nuclei, and other cellular components are removed as completely as possible from the tissue in order to obtain the purest extracellular matrix possible. Any cells and cellular components remaining in the tissue could potentially cause an unwanted calcification of the biological implant material. The decellularization should be performed in a manner that is so gentle that the structure of the extracellular matrix and the collagen fibers in the extracellular matrix remain as unaffected as possible while ensuring that all cells and cell components contained therein are removed from the tissue.

Another possible preparation step is that of cross-linking the extracellular matrix, in particular the collagen fibers, of the tissue. After decellularization, preferably all cellular components have been removed from the tissue and the biological material consists of only the extracellular matrix. In the case of pericardial tissue, the extracellular matrix is formed primarily of collagen fibers. In order to obtain biological material having the most optimal mechanical properties possible and to prevent rejection reactions by the receiving body, the collagen fibers are cross-linked by means of a suitable cross-linking agent via the incorporation of chemical bonds. The cross-linking agent binds to free amino groups of the collagen fibers and forms chemically stable compounds between collagen fibers. A biological material having long-term stability is thereby obtained from the three-dimensionally arranged collagen fibers, wherein this biological material is no longer recognized as foreign biological material. The stability and strainability of the tissue is markedly increased by means of the three-dimensional cross-linking or linking of the individual collagen fibers via the cross-linking agent. This is decisive, in particular, in the case of use as tissue of a heart valve, where the tissue is intended to open and close, in brief intervals, as a valve.

The thusly treated tissue is secured to a support body, usually via suturing. The support body or the support frame can be implanted using surgical techniques. As an alternative, the support frame is self-expanding or can be expanded by means of a balloon such that the heart valve prosthesis can be guided, in the compressed state, to the site of implantation by means of a catheter and can be implanted inside the natural valve.

According to the prior art, such heart valve prostheses, which can be implanted by means of a catheter, are stored in a storage solution, i.e., in the moist state. The storage solution is used for the sterile stabilization of the biological tissue. For implantation, the heart valve prosthesis must then be removed from the storage solution in the surgical suite and, after a plurality of rinsing processes, must be mounted on the catheter. This assembly of the heart valve prosthesis in the surgical suite itself is complex and requires a great deal of work. In addition, whether or not the assembly is carried out correctly depends on the skills of the particular surgical team.

Approaches are therefore known in the prior art for drying such biological tissue, and for processing and sterilizing said biological tissue in the dried state. This would make it possible to sterilize, sterile-package, and pre-assemble a total system comprising a catheter and a pre-assembled heart valve prosthesis.

A method for the preparation of a heart valve prosthesis, which includes the processing of dried, biological material, is disclosed in U.S. Pat. No. 8,105,375. According to the method disclosed therein, the biological tissue is fixed or cross-linked with an aldehyde-containing solution (e.g., glutaraldehyde or formaldehyde solution) and, before drying, is treated with at least one aqueous solution, which contains at least one biocompatible and non-volatile stabilizer. The stabilizers that are disclosed are hydrophilic hydrocarbons comprising a plurality of hydroxyl groups and, as examples, water-soluble sugar alcohols such as glycerol, ethylene glycol or polyethylene glycol are mentioned.

SUMMARY OF THE INVENTION

The problem addressed by the present invention is that of designing a method for the preparation of biological tissue for dry use in an implant, and an implant, such that a high level of dimensional stability is achieved as well as targeted protection of the tissue structure, coupled with a lower risk of calcification.

According to the invention, before drying and after a pretreatment for cross-linking with an aldehyde-containing solvent, in particular a glutaraldehyde- or formaldehyde-containing solvent, the tissue is subjected to a dimensional and structural stabilization step in which the tissue is exposed to a first solution, which contains polyethylene glycol, and is exposed to a second solution, which contains glycerol, wherein the tissue is exposed either to the two solutions one after the other in any order, or is exposed to both solutions simultaneously, as the first solution mixture.

Surprisingly, targeted protection of the structure of the biological tissue is obtained by means of the targeted selection and combination of polyethylene glycol and glycerol. By means of the targeted combination of polyethylene glycol and glycerol, a macroscopic dimensional stability of the treated biological tissue during drying is achieved, as in the prior art, but also the microscopic tissue structures are protected and maintained by means of the stabilization of the hydrogen bridges. In addition, specific protection of the biological tissue to be dried is obtained by means of the combination. Glycerol and polyethylene glycol penetrate the tissue and stabilize the structure. Polyethylene glycol becomes attached, in additionally concentrated form, on the surface of the tissue and protects this tissue from external influences. In addition, the targeted use of polyethylene glycol in combination with glycerol results in a marked reduction of the risk of calcification of the implanted tissue.

According to a particularly preferred embodiment of the invention, the tissue is also exposed—before drying—to at least one third solution, which contains polyethylene glycol having a mean molecular weight, in each case, that differs from that of the previous solution, wherein the tissue is either exposed to the solutions one after the other in any order, or is exposed thereto simultaneously, as a solution mixture. Preferably, the mean molecular weight of the polyethylene glycol of the third solution is higher than the mean molecular weight of the polyethylene glycol of the first solution. In this embodiment of the invention, the solutions can be combined in any manner. This includes the use of three separate solutions, a separate solution, and a solution mixture, as well as the use of only one solution mixture containing all three solutions. Likewise, in some embodiments, it can be advantageous to use additional solutions that contain polyethylene glycol.

The advantages of the invention are particularly effective in this preferred embodiment. This embodiment is based on the finding made by the inventors that, the penetration depth of polyethylene glycol into the biological tissue depends on the molecular weight. It is suspected that this is due to the viscosity changing with the molecular weight. The use of a first polyethylene glycol-containing solution and a third solution, which contains polyethylene glycol having a mean molecular weight that differs from that of the first solution, induces stabilization effects at different tissue depths. In this embodiment of the invention, it is therefore possible, in particular, to retain and stabilize the microscopic tissue structures.

Preferably, the first solution contains polyethylene glycol having a mean molecular weight between 200 g/mol and 6000 g/mol, in particular between 200 g/mol and 1000 g/mol.

According to a particularly preferred embodiment of the invention, the first solution contains polyethylene glycol having a mean molecular weight between 400 g/mol and 600 g/mol.

In another embodiment of the invention, the third solution contains polyethylene glycol having a mean molecular weight between 1000 g/mol and 6000 g/mol, in particular having a mean molecular weight of 4000-6000 g/mol.

According to a preferred embodiment of the invention, the preparation of the biological tissue is carried out either as treatment with a first solution mixture, which comprises a first solution containing polyethylene glycol having a mean molecular weight between 400 g/mol and 600 g/mol and a second solution containing glycerol, or as treatment with a second solution mixture, which comprises a first solution containing polyethylene glycol having a mean molecular weight between 200 g/mol and 1000 g/mol, a second solution containing glycerol, and a third solution containing polyethylene glycol having a mean molecular weight between 1000 g/mol and 6000 g/mol, in particular having a mean molecular weight of 4000-6000 g/mol.

In an alternative embodiment of the invention, the biological tissue is first exposed to a first solution containing polyethylene glycol having a mean molecular weight between 200 g/mol and 6000 g/mol and, subsequently, to a second solution containing glycerol.

In another embodiment of the invention, the biological tissue is first exposed to a third solution containing polyethylene glycol having a mean molecular weight between 1000 g/mol and 6000 g/mol, in particular having a mean molecular weight of 4000-6000 g/mol, and, subsequently, to a first solution containing polyethylene glycol having a mean molecular weight between 200 g/mol and 1000 g/mol, followed by a second solution, which contains glycerol.

In an embodiment that has proven to be preferable, the biological tissue is first subjected to a treatment with the second glycerol-containing solution, subsequently to a treatment with the first solution containing polyethylene glycol having a low mean molecular weight in the range of 200 g/mol to 400 g/mol, followed by a treatment with a third solution, which contains polyethylene glycol having a slightly higher mean molecular weight. In this embodiment, the glycerol of the second solution first deeply penetrates the tissue, the polyethylene glycol of the first solution penetrates the regions close to the surface, and the polyethylene glycol of the third solution induces a sealing of the surface. In this embodiment, the two polyethylene glycol-containing solutions can also be the same.

Expediently, the tissue is exposed to the first or the third solution or to the first or the second solution mixture for 1 to 12 hours, preferably for 2 to 6 hours, particularly preferably for 2 hours. In this case, polyethylene glycol is advantageously present in the first or the third solution or in the first or the second solution mixture in a concentration of 5 vol % to 60 vol %, preferably of 10 vol % to 40 vol %. Glycerol is expediently contained in the second solution or in the first or the second solution mixture in a concentration of 5 vol to 50 vol %, preferably 5 vol % to 30 vol %.

Within the scope of this application, the unit of measure "vol %" refers to a percentage of volume. A 100 ml solution having 5 vol % of polyethylene glycol therefore contains 5 ml of pure polyethylene glycol. The unit of measure "weight %" refers to a percentage of weight, within the scope of this application. A 100 g solution having 0.9 weight % of sodium chloride therefore contains 0.9 g sodium chloride.

Preferably, the biological tissue was subjected to a pretreatment comprising an optional decellularization with a suitable detergent, preferably a solution containing surfactin and deoxycholic acid, and a subsequent cross-linking, preferably with a glutaraldehyde-containing solution.

The method described in this application is suitable for the preparation of native, cross-linked, decellularized or non-decellularized tissue.

With regard to the device, the stated problem is solved by an implant comprising biological tissue, which was subjected to the method for preparation according to the invention and was dried.

In this connection, the drying of the tissue is designed such that a slow and gentle withdrawal of the water, in the liquid state, from the tissue is ensured. This is advantageously achieved by means of the controlled reduction of the ambient humidity of the biological tissue in a desiccator or a climate-controlled chamber under controlled settings of the parameters of the ambient atmosphere of the biological tissue.

The implant is preferably a heart valve prosthesis, which comprises an artificial heart valve made of biological tissue and/or a seal made of biological tissue, which is secured on an expandable or self-expanding support frame, which can be implanted by means of a catheter, preferably being secured thereon via suturing.

DETAILED DESCRIPTION OF PREFERRED EMBODIMENTS

Figure 1:
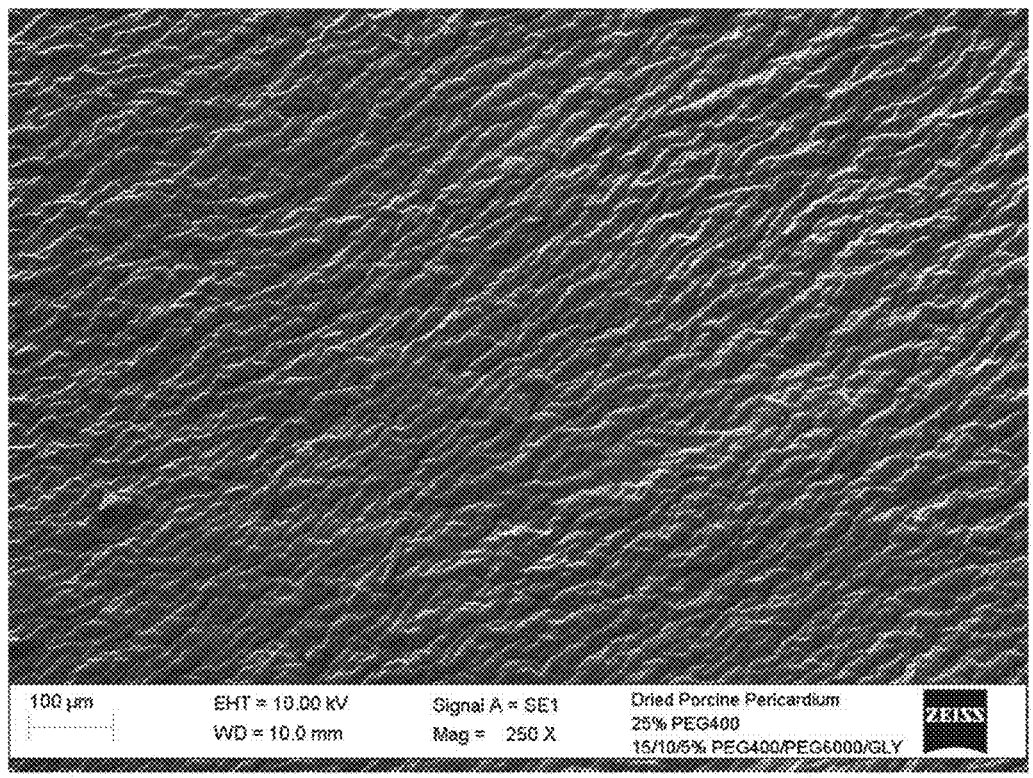
FIG. 1 shows an electron microscopic image of a porcine pericardial tissue according to Example 1.
Figure 2:
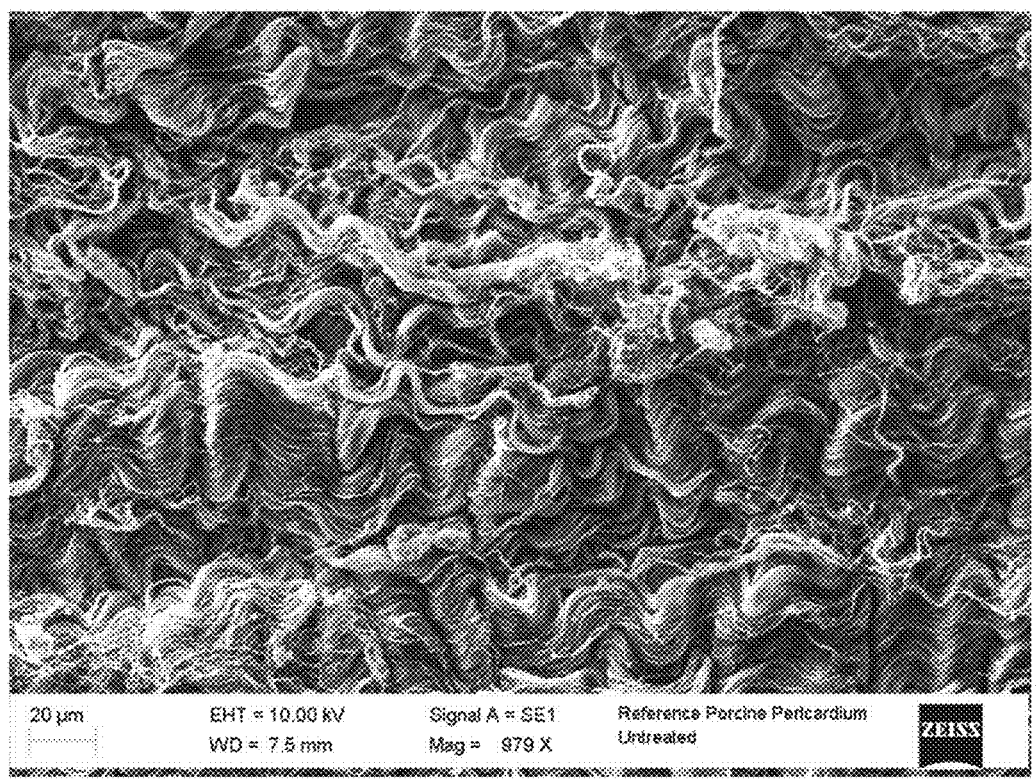
FIG. 2 shows an untreated, cross-linked pericardium, as the reference.

The invention will be explained in greater detail in the following on the basis of three exemplary embodiments and a comparison—depicted in FIGS. 1 and 2—of a dried biological tissue according to one exemplary embodiment of the invention with the prior art.

Example 1

Example 1 discloses an embodiment of the method according to the invention for the preparation of porcine pericardium with subsequent drying. FIG. 1 shows a porcine pericardial tissue in the dried state after a treatment according to example 1. A sealing and stabilization of the surface structure resulting from the treatment with the stabilizers is shown very clearly in the electron microscopic image. The untreated reference tissue shown in FIG. 2 comprises exposed collagen structures, which are present in the unsealed state.

First, a pericardium is removed from a freshly slaughtered pig in a slaughterhouse and is stored in a solution of 0.9 weight % of sodium chloride, which contains penicillin and/or streptomycin, for 2 hours at a temperature of 4° C. In the next step, fat and connective tissue are separated from the pericardial tissue in moist conditions (solution of 0.9 weight % of sodium chloride), and the pericardial tissue is trimmed to the proper size.

Next, the tissue is rinsed (100 ml solution of 0.9 weight % of sodium chloride, accompanied by gentle movement), cross-linked (48 hours in 100 ml solution of 0.6 weight % of glutaraldehyde solution (glutaraldehyde in buffered saline solution at 4-8° C. (DPBS solution from the company Lonza; DPBS w/o Ca++/Mg++; Art. No 17-512)), wherein this solution then acts for 14 days at room temperature and is replaced with a similar, fresh solution once every 48 hours), and is then rinsed again (rinsed for 10 min in 100 ml solution of 0.9 weight % of sodium chloride at 37° C., accompanied by gentle movement, repeat 6 times).

The thusly treated, cross-linked biological tissue is then subjected to an embodiment of the dimensional and structural stabilization step according to the invention.

In this embodiment, the biological tissue is subjected to a first rinsing for 10 min in 100 ml of an aqueous solution of 25 vol %, of polyethylene glycol (containing polyethylene glycol having a mean molecular weight of 400 g/mol) at 37° C., repeated 3 times.

Next, the biological tissue is exposed to a second solution mixture for 2 hours at a temperature of 37° C. In this embodiment of the invention, the second solution mixture comprises an aqueous solution containing polyethylene glycol having a mean molecular weight of 400 g/mol in a concentration of 15 vol. % of polyethylene glycol having a mean molecular weight of 6000 g/mol in a concentration of 10 vol % and glycerol in a concentration of 5 vol %.

The thusly stabilized biological tissue is then dried in a desiccator for 24 hours, using a silical gel as the desiccant. The thusly obtained, dried, biological tissue can either be further processed or stored in the desiccator.

Within the scope of this application, a desiccator refers to a closed vessel, which contains an active desiccant and has minimal humidity in the interior thereof.

As an alternative, the drying can also to place in a climate-controlled chamber having an adjustable temperature and humidity.

Example 2

Similar to example 1, a pericardium is removed from a pig, stored for 2 hours at a temperature of 4° C. in a solution of 0.9 weight % of sodium chloride, which contains penicillin and/or streptomycin, is prepared in moist conditions (solution of 0.9 weight % of sodium chloride) with removal of fat and connective tissue, is trimmed to size, and is subsequently rinsed with 100 ml of a solution of 0.9 weight % of sodium chloride, accompanied by gentle movement.

The thusly obtained pericardium is then subjected to gentle decellularization and subsequent cross-linking. The following steps are carried out:

decellularization in 100 ml surfactin/desoxycholic acid solution (0.06 weight % of surfactin and 0.5 weight % of desoxycholic acid in a solution of 0.9 weight % of sodium chloride) for 20 hours at 37° C.

rinsing with 100 ml of a solution of 0.9 weight % of sodium chloride (6 times, accompanied by gentle movement, for 10 min)

treatment with a DNase solution for 12 hours at 37° C.

rinsing with 100 ml of a solution of 0.9 weight % of sodium chloride (8 times, accompanied by gentle movement, for 10 min)

rinsing with 100 ml of a solution of 70 vol % of ethanol (once, for 10 min)

rinsing with 100 ml of a solution of 0.9 weight % of sodium chloride cross-linking with glutaraldehyde (48 hours in 100 ml of a solution of 0.6 weight % of glutaraldehyde (glutaraldehyde in buffered saline solution at 4-8° C. (DPBS solution from the company Lonza; DPBS w/o Ca++/Mg++; Art. No. 17-512)), wherein this solution then acts for 11 days at room temperature and is replaced with a similar, fresh solution once every 48 hours)

rinsing with 100 ml of a solution of 0.9 weight %, of sodium chloride (6 times, accompanied by gentle movement, for 10 min)

In this embodiment of the invention, the thusly produced, decellularized and cross-linked pericardial tissue is stabilized in three steps. First, the tissue is rinsed with 100 ml of an aqueous solution of 25 vol % of polyethylene glycol (containing polyethylene glycol having a mean molecular weight of 400 g/mol at 37° C., 3 times for 10 min). Next, the tissue is exposed to an aqueous solution containing 20 vol % of polyethylene glycol having a mean molecular weight of 400 g/mol and 10 vol % of glycerol for 2 hours at 37° C., accompanied by gentle movement. This is followed by a treatment with an aqueous solution containing 20 vol % of polyethylene glycol having a mean molecular weight of 6000 g/mol and 10 vol % of glycerol, accompanied by gentle movement, at a constant temperature for 2 hours.

The thusly stabilized biological tissue is then dried in a desiccator for 24 hours, using a silical gel as the desiccant, and is then further processed.

Example 3

In the embodiment according to example 3, already cross-linked porcine pericardial tissue is prepared (stabilized and dried) using the following method:

rinsing with 100 ml of a solution of 0.9 weight % of sodium chloride (6 times, accompanied by gentle movement, for 10 min, at room temperature), rinsing with 100 ml of an aqueous solution of 40 vol % of glycerol (3 times, accompanied by gentle movement, for 20 min at 37° C.), placing the pericardial tissue in an aqueous solution containing 30 vol % of polyethylene glycol having a mean molecular weight of 400 g/mol and 10 vol % of glycerol for 2 hours at 37° C., accompanied by gentle movement, placing the pericardial tissue in an aqueous solution containing 30 vol % of polyethylene glycol having a mean molecular weight of 6000 g/mol and 10 vol % of glycerol for 2 hours at 37° C., accompanied by gentle movement, and drying in the dessicator for 24 hours, using silica gel as the dessicant.

What is claimed is:

1. A method of preparing biological tissue for use as a component of a heart valve prosthesis comprising pretreating the tissue, and stabilizing the pretreated tissue, characterized in that, the step of pretreating the tissue comprises crosslinking the tissue with an aldehyde-containing solvent, wherein the aldehyde is glutaraldehyde or formaldehyde; and the step of stabilizing the pretreated tissue comprises exposing the tissue to three solutions for dimensional and structural stabilization, wherein a first solution contains polyethylene glycol having a mean molecular weight between 200 g/mol and 400 g/mol, a second solution contains glycerol, and a third solution contains polyethylene glycol having a mean molecular weight between 1,000 g/mol and 6,000 g/mol, wherein the tissue is exposed to the first and second solutions before the third solution.

2. The method according to claim 1, characterized in that the tissue is exposed to the first or the third solution for 1 to 12 hours.

3. The method according to claim 1, characterized in that the polyethylene glycol is present in the first or the third solution in a concentration of 5 vol % to 60 vol %.

4. The method according to claim 1, characterized in that glycerol is contained in the second solution in a concentration of 5 vol % to 50 vol %.

5. The method according to claim 1, further comprising decellularizing the tissue with a suitable detergent prior to the cross-linking.

6. The method according to claim 1, further comprising drying the stabilized tissue.

7. The method according to claim 1, characterized in that the polyethylene glycol in the third solution has a mean molecular weight of 4,000-6,000 g/mol.

8. The method according to claim 2, characterized in that the tissue is exposed to the first or the third solution for 2 to 6 hours.

9. The method according to claim 3, characterized in that the polyethylene glycol is present in the first or the third solution in a concentration of 10 vol % to 40 vol %.

10. The method according to claim 4, characterized in that glycerol is contained in the second solution in a concentration of 5 vol % to 30 vol %.

11. The method according to claim 5, characterized in that the detergent is a solution containing surfactin and deoxycholic acid.

12. The method according to claim 1, wherein the third solution contains 30 vol % polyethylene glycol.

13. A method of preparing biological tissue for use as a component of a heart valve prosthesis, the method comprising: crosslinking the tissue with glutaraldehyde or formaldehyde; treating the crosslinked tissue in an aqueous solution of polyethylene glycol and glycerol, the polyethylene glycol having a mean molecular weight between 200 g/mol and 1,000 g/mol; and placing the treated tissue in an aqueous solution of 30 vol % polyethylene glycol having a mean molecular weight between 1,000 g/mol and 6,000 g/mol and 10% glycerol.

14. The method according to claim 13, wherein the polyethylene glycol between 200 g/mol and 1,000 g/mol is between 400 g/mol and 600 g/mol.

15. The method according to claim 13, wherein the polyethylene glycol between 200 g/mol and 1,000 g/mol is between 200 g/mol and 400 g/mol.

16. The method according to claim 15, wherein the polyethylene glycol between 200 g/mol and 400 g/mol is at 30 vol %.

* * * * *